United States Patent
Sood et al.

(10) Patent No.: US 7,256,019 B2
(45) Date of Patent: Aug. 14, 2007

(54) TERMINAL PHOSPHATE BLOCKED NUCLEOSIDE POLYPHOSPHATES

(75) Inventors: Anup Sood, Flemington, NJ (US); Shiv Kumar, Belle Mead, NJ (US); Carl Fuller, Berkeley Heights, NJ (US); John Nelson, Hillsborough, NJ (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 517 days.

(21) Appl. No.: 10/651,355

(22) Filed: Aug. 29, 2003

(65) Prior Publication Data

US 2004/0048300 A1 Mar. 11, 2004

Related U.S. Application Data

(63) Continuation-in-part of application No. 10/113,030, filed on Apr. 1, 2002, and a continuation-in-part of application No. 10/113,025, filed on Apr. 1, 2002, and application No. 10/358,818, Feb. 5, 2003, and application No. 10/230,576, Aug. 29, 2002.

(60) Provisional application No. 60/406,892, filed on Aug. 29, 2002, provisional application No. 60/406,893, filed on Aug. 29, 2002, provisional application No. 60/404,894, filed on Aug. 29, 2002, provisional application No. 60/315,798, filed on Aug. 29, 2001.

(51) Int. Cl.
C12Q 1/68 (2006.01)
C12P 19/34 (2006.01)
C07H 21/04 (2006.01)

(52) U.S. Cl. .................. 435/91.1; 435/6; 435/91.2; 536/23.1; 536/24.3

(58) Field of Classification Search .............. 435/6, 435/91.1, 91.2; 536/23.1, 24.3
See application file for complete search history.

(56) References Cited

U.S. PATENT DOCUMENTS

| 4,711,955 A | 12/1987 | Ward et al. |
| 4,828,979 A | 5/1989 | Klevan et al. |
| 5,772,688 A | 6/1998 | Muroki |
| 5,848,985 A | 12/1998 | Muroki |
| 5,849,487 A | 12/1998 | Hase et al. |

(Continued)

FOREIGN PATENT DOCUMENTS

WO WO96/22297 7/1996

(Continued)

OTHER PUBLICATIONS

Newton, C. R., et al. "The Production of PCR Products with 5' Single-Stranded Tails Using Primers that Incorporate Novel Phosphoramidite Intermediates" Nucleic Acid Research, Oxford University Press, Surrey, GB, vol. 21, No. 5, 1993, pp. 1155-1162.

(Continued)

*Primary Examiner*—Jezia Riley
(74) *Attorney, Agent, or Firm*—Yongganf Ji

(57) ABSTRACT

The present invention describes terminal phosphate blocked nucleoside polyphosphates that are stable at high temperature and their use in nucleic acid amplification and analysis. Current invention further describes charge modified terminal phosphate blocked nucleoside polyphosphates for improved incorporation and direct loading of nucleic acid sequencing reactions onto separating media.

14 Claims, 5 Drawing Sheets

U.S. PATENT DOCUMENTS

| | | | |
|---|---|---|---|
| 6,044,286 | A | 3/2000 | Ogama |
| 6,083,253 | A | 7/2000 | Ogama |
| 6,187,286 | B1 | 2/2001 | Elmaleh et al. |
| 6,306,607 | B2 * | 10/2001 | Williams ............... 435/6 |
| 2004/0176803 | A1 | 9/2004 | Whelan et al. |
| 2004/0176805 | A1 | 9/2004 | Whelan et al. |

FOREIGN PATENT DOCUMENTS

| | | |
|---|---|---|
| WO | WO99/16832 | 4/1999 |
| WO | WO 02/40126 | 5/2002 |
| WO | WO 03/020734 | 3/2003 |
| WO | WO 03/020891 | 3/2003 |
| WO | WO 2004/080531 A2 | 9/2004 |

OTHER PUBLICATIONS

Dyatkina, N., et al. "Modified Triphosphates of carbocyclic nucleoside analogues: synthesis, stability towards alkaline phosphatase and substrate properties for some DNA polymerases" Bioorganic and Medicinal Chemistry Letters, Oxford, GB, vol. 6, No. 22, Nov. 19, 1996, pp. 2639-2642.

Su, S-H., et al. "Novel non-nucleosidic phosphoramidites for oligonucleotide modification and labeling" Bioorganic and Medicinal Chemistry Letters, Oxford, GB, vol. 7, No. 13, Jul. 8, 1997, pp. 1639-1644.

Arzumanov Andrey, A., et al. "Gamma-Phosphate-substituted 2'-deoxynucleoside 5'-triphosphates as substrates for DNA polymerases" Journal of Biological Chemistry, vol. 271, No. 40, 1996, pp. 24389-24394.

* cited by examiner

Normal terminator sequence ladder

Phosphate blocked terminator sequence ladder

TERMINAL PHOSPHATE BLOCKED NUCLEOSIDE POLYPHOSPHATES

CROSS REFERENCE TO RELATED APPLICATIONS

This application claims priority to United States provisional patent application Nos. 60/406,892, 60/406,893, and 60/406,894 all filed Aug. 29, 2002 and to U.S. patent application Ser. No. 10/230,576 filed Aug. 29, 2002 and 10/358,818 filed Feb. 5, 2003. This application is a continuation-in-part of U.S. patent application Ser. No. 10/113,030 and 10/113,025 both filed Apr. 1, 2002, all of which claim the benefit of United States provisional patent application No. 60/315,798 filed Aug. 29, 2001. The disclosures of these applications are incorporated herein by reference in their entireties.

FIELD OF INVENTION

The present invention relates to terminal phosphate blocked nucleoside polyphosphates that are stable at high temperature and their use in nucleic acid amplification and analysis. Current invention further describes charge modified terminal phosphate blocked nucleoside polyphosphates for improved incorporation and direct loading of nucleic acid sequencing reactions onto separating media.

BACKGROUND OF INVENTION

DNA amplification by a number of amplification methods is performed at high temperatures. For example, in PCR, repeated cycles of denaturation at 95° C., annealing around 60° C. and extension around 70° C. causes significant breakdown of the dNTP's. This may significantly affect the yield of product in later cycles. Other amplification methods such as RCA and NASBA, although isothermal, also are conducted at higher temperatures. In case of NASBA, which is performed at 41° C., the stability of nucleotides may not be very critical. However RCA may be conducted at higher temperature depending upon the polymerase used and the complexity of sequence to be amplified. Stability of nucleotides can be an issue under these conditions. It is therefore desirable to have nucleotides that can survive this repeated cycling of temperature or prolonged heating at a constant yet high temperature and hence continue to give high product yields even in later cycles of amplification and possibly cut down the number of cycles/time required to achieve desirable amplification.

The sequence of nucleotide bases in a DNA molecule can be determined in a variety of ways. The chain termination method generally involves synthesizing DNA complementary to the template strand to be sequenced by extending a primer able to hybridize to a portion of that template strand with a DNA polymerase. During the synthesis reaction, deoxynucleoside triphosphates (dNTP's) are incorporated to form a DNA fragment until a chain terminating agent, for example, a dideoxynucleoside triphosphate (ddNTP) is incorporated. Incorporation of a ddNTP prevents further DNA synthesis (a process called chain termination). The size of each DNA fragment synthesized in this procedure is then determined by gel electrophoresis and this information used to determine the sequence of nucleotides in the original template DNA. For example, Tabor and Richardson, U.S. Pat. No. 4,795,699, the entire disclosure of which is incorporated herein, describes a two step sequencing method in which an unlabeled primer is labeled in a labeling step, and then extended in the presence of excess dNTPs and a ddNTP in a chain termination step. In the labeling step, a low concentration of dNTPs is provided (one being labeled) to allow a small amount of primer extension.

In the dideoxy sequencing method, the primer may be labeled, for example with 32P, by a process using a polynucleotide kinase. Such labeling allows detection of extended primers after gel electrophoresis by auto-radiography of the resulting gel. Alternatively, a labeled dNTP may be incorporated during the process of DNA synthesis, and the presence of such labeled dNTPs detected by autoradiography or other means. To this end, the dNTP may be labeled either radioactively with 32P or 35S. In another procedure, the primer can be labeled with one or more fluorescent moieties for detection by fluorescence. In yet another procedure, the ddNTP may be labeled, for example, with a fluorescent marker.

In a sequencing reaction, the labeled dNTPs or ddNTPs partially decompose, most likely due to the thermocycling conditions, and generate labeled by-products which migrate in the separating media, thus interfering with interpretation of the true sequencing fragments. For example, labeled dNTP or ddNTP decomposition products and unreacted terminators may appear on sequencing gels or electropherogram as peaks or blobs (FIG. 1, Lanes 3 and 4, blobs result when sequencing products containing conventional terminators are directly loaded onto, an electrophoretic gel). At the present time, this problem is addressed by precipitation of the sequencing products using e.g., ethanol precipitation prior to loading (FIG. 1, lanes 1 and 2). While this reduces the contamination somewhat, the procedure is time consuming and creates a bottleneck for high throughput sequencing applications.

Thus, a process is needed for improving the clarity of sequencing data. Ideally, such a process would reduce sample preparation time and result in improved sequencing throughput. Moreover, such a method would also be economical to use. These and other concerns are addressed in greater detail below.

Recently, charge modified nucleoside-triphosphates that are either highly negatively charged so that they (or any fragmentation products) move well ahead of the sequence product fragments or highly positively charged so that they (or any fragmentation products) move in the opposite direction of the sequencing fragment when separated on a sequencing gel, have been described (WO 01/19841). These nucleotides have a string of negatively or positively charged moieties attached to the base. These nucleotides once incorporated, due to the presence of string of charges on the base, significantly affect the mobility of sequencing fragments. It is desirable to have modified nucleoside triphosphates that are either highly negatively charged or net positively charged, but after incorporation have same charge as the natural nucleotides. Therefore, mobility of the sequencing products is not affected. Even when mobility is not an issue, it is desirable to have more stable nucleoside triphosphate so that any possible complications from breakdown products are prevented.

SUMMARY OF INVENTION

One aspect of the instant disclosure pertains to use of terminal phosphate blocked nucleoside polyphosphates (Structure 1) in high temperature amplification methods such as PCR to enhance yield of amplified product. Another aspect describes labeled nucleoside polyphosphates with a blocking group on the terminal phosphate and their use in sequencing and other genotyping methods requiring high temperature or temperature cycling.

The present invention further includes a nucleic acid amplification and/or detection kit wherein the kit includes: at least one thermally stable terminal-phosphate-blocked nucleotides according to the following formula:

Z—X—S—B—L (Structure 1)

wherein Z is a terminal block consisting of an organic moiety. The terminal block may be linear or branched acyclic or cyclic alkyl, alkenyl, alkynyl, aromatic, heterocyclic moiety or a detectable label with or without a linker and may contain atoms such as C, H, N, O, P, S and halogen. Z may also be optionally modified to contain additional negative charges or positively charged moieties. In latter case amount of positive charge added in conjunction with any other positive charge on the molecule is sufficient to make the whole entity net positively charged;

X is a polyphosphate chain with at least 3 phosphate or modified phosphate groups with the proviso that such a modification does not prevent the incorporation of this nucleoside polyphosphate into a DNA or RNA polymer;

S is a natural or modified sugar, a carbocycle or an acyclic linker;

B is a natural or modified heterocycle. Suitable base analogs include but are not limited to those disclosed in WO 99/06422 and WO 97/28177, the entire disclosures of which are hereby incorporated by reference;

L is H or a linker moiety. The linker may be H, linear or branched, cyclic or acyclic alkyl, alkenyl, or alkynyl, aromatic, heterocyclic and may contain atoms such as C, H, N, O, S and halogen; and L, B, S, X, or Z are substituted with a moiety which may impart additional negative charge or a net positive charge to Structure 1 at physiological or nucleic acid sequencing conditions.

The linker may optionally be substituted with a label, (also referred to as a "reporter or signal moiety"). The label may be a moiety such as a fluorescent tag, an energy transfer (ET) label, a radioisotope, an electrochemical tag, a mass spectrometry tag, a Raman tag, a hapten, a chemiluminescent group, an enzyme, a chromophore, and two or more labels. The label may also be charged, e.g. Cy3.5, Cy5.5, carboxyfluorescein, or a dye attached to a charged moiety, e.g., carboxyfluorescein attached to cysteic acid or similar charged species. Methods for making these and other similar compounds are known in the art and are disclosed in Alexandrova LA et. al., Nucleic Acids Research, 1998, 26, 778-786, Arzumanov AA et. al., J. Biological Chemistry, 1996, 271, 24389-24394. U.S. patent application Ser. No, 90/018,695, and PCT patent application GB98/00978, the entire disclosures of which are hereby incorporated by reference.

The molecule may be modified with a moiety which imparts an additional negative charge or a net positive charge to Structure 1 at physiological or nucleic acid sequencing or amplification conditions. The moiety may be any charged species that alters the electrophoretic mobility of the Structure, e.g., α-sulfo-β-alanine, cysteic acid, sulfonic acids, carboxylates, phosphates, phosphodiesters, phosphonates, amines, quarternized amines, and phosphonium moieties. The moiety (referred to as a "mobility modifier") may be attached between the linker and label, between the base and linker, and may be attached only to the sugar or only to the linker. It may also be attached between terminal phosphate and may in fact be the terminal block. It may also be attached between a label and the terminal block or only to the terminal block or only to the label on terminal block. The molecule may also contain multiple linkers and moieties that are alternatively spaced together.

DETAILED DESCRIPTION OF INVENTION

Figure 1:
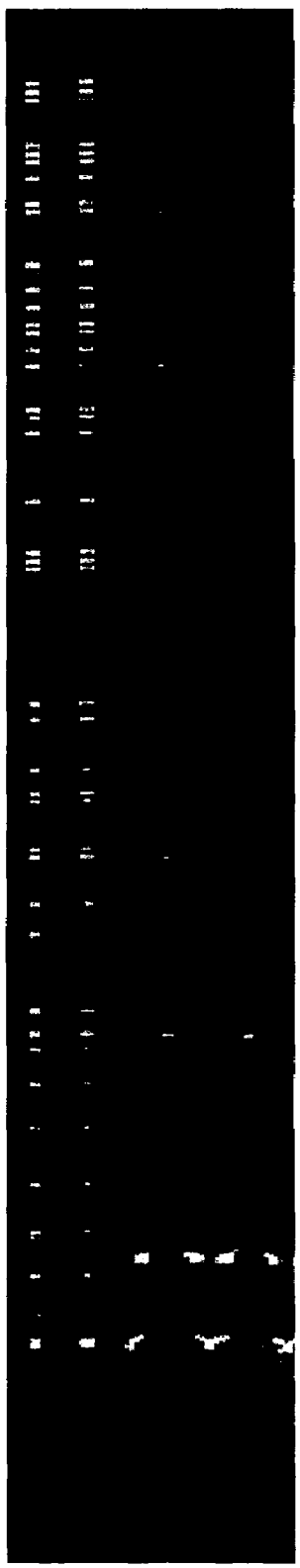
FIG. 1 is a gel image of an ET terminator DNA sequencing reaction loaded either after ethanol precipitation (Lanes 1 and 2) or directly loaded (Lanes 3 and 4) onto the sequencing gel.

The term "nucleoside" as defined herein is a compound including a purine deazapurine, or pyrimidine base linked to a sugar or a sugar substitute, such as a carbocyclic or acyclic linker at the 1' position or equivalent position and includes 2'-deoxy and 2'-hydroxyl, 2', 3'-dideoxy forms, as well as other substitutions.

The term "nucleotide" as used herein refers to a phosphate ester of a nucleoside, wherein the esterification site typically corresponds to the hydroxyl group attached to the C-5 position of the pentose sugar.

The term "oligonucleotide" includes linear oligomers of nucleotides or derivatives thereof, including deoxyribonucleosides, ribonucleosides, and the like. Throughout the specification, whenever an oligonucleotide is represented by a sequence of letters, the nucleotides are in the 5'→3' order from left to right where A denotes deoxyadenosine, C denotes deoxycytidine, G denotes deoxyguanosine, and T denotes thymidine, unless noted otherwise.

The term "primer" refers to a linear oligonucleotide that anneals in a specific way to a unique nucleic acid template sequence and allows for amplification of that unique sequence.

For purposes of the methods of the present invention, useful carbocyclic moieties have been described by Ferraro, M. and Gotor, V. in Chem Rev. 2000, volume 100, 4319-48. Suitable sugar moieties are described by Joeng, L. S. et al., in J Med. Chem. 1993, vol. 356, 2627-38; by Kim H. O. et al., in J Med. Chem. 193, vol. 36, 30-7; and by Eschemnosser A., in Science 1999, vol. 284, 2118-2124. Moreover, useful acyclic moieties have been described by Martinez, C. I., et al., in Nucleic Acids Research 1999, vol. 27, 1271-1274; by Martinez, C. I., et al., in Bioorganic & Medicinal Chemistry Letters 1997, vol. 7, 3013-3016; and in U.S. Pat. No. 5,558,91 to Trainer, G. L. Structures for these moieties are shown below, where for all moieties R may be H, OH, NHR, lower alkyl and aryl; for the sugar moieties X and Y are independently O, S, or NH; and for the acyclic moieties, X=O, S, NH, NR.

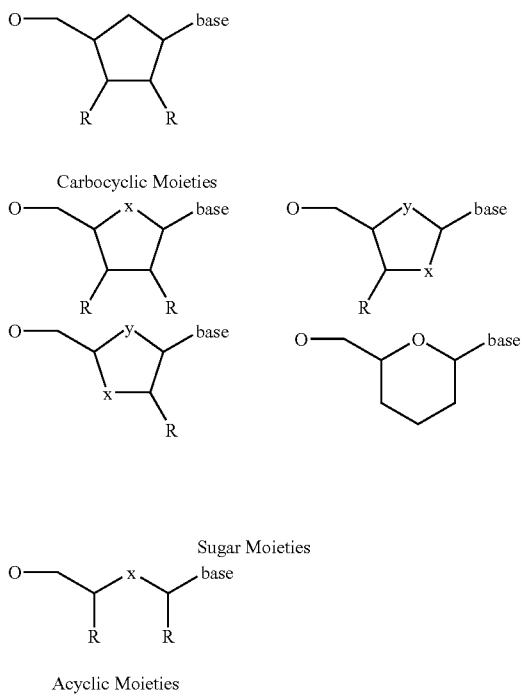

Carbocyclic Moieties

Sugar Moieties

Acyclic Moieties

In certain embodiments, the sugar moiety may be selected from the following: ribosyl, 2'-deoxyribosyl, 3'-deoxyribosyl, 2',3'-dideoxyribosyl, 2',3'-didehydrodideoxyribosyl, 2'-alkoxyribosyl, 2'-azidoribosyl, 2'-aminoribosyl, 2'-fluororibosyl, 2'-mercaptoriboxyl, 2'-alkylthioribosyl, 3'-alkoxyribosyl, 3'-azidoribosyl, 3'-aminoribosyl, 3'-fluororibosyl, 3'-mercaptoriboxyl, 3'-alkylthioribosyl carbocyclic, acyclic and other modified sugars. In other embodiments, the 3'-position has a hydroxyl group, required for chain elongation.

Moreover, in Structure 1 above, the base may include uracil, thymine, cytosine, 5-methylcytosine, guanine, 7-deazaguanine, hypoxanthine, 7-deazahypoxanthine, adenine, 7-deazaadenine, 2,6-diaminopurine or analogs thereof.

The present invention pertains to the use of terminal phosphate blocked nucleic acid polyphosphates which have enhanced stability at high temperature than the corresponding unblocked nucleic acid polyphosphates. These include deoxynucleoside polyphosphates and ribonucleoside polyphosphates blocked at the terminal position. These also include terminal phosphate blocked dideoxynucleoside polyphosphates or nucleoside terminators, which do not break down significantly during sequencing reactions and migrate on separation media at different rates than the sequencing reaction products. This results in improved sequence data. Such nucleic acid terminators also allow for the direct loading of nucleic acid sequencing reactions onto separating media. To achieve this goal, the terminator phosphate moiety is modified to stabilize the terminator molecule. The unreacted terminators move faster (negatively charged). It is further possible to affect mobility by adding additional negative charges to the terminator or making the terminator overall positively charged by adding a number of positive charges to the structure by modification. The latter is also desirable as it has been found that positively charged nucleoside triphosphates are better substrates for polymerases than the parent compounds (Finn et. al., Nucleic Acids Research (2003) 31, 4769-4778).

One embodiment of the terminal phosphate blocked nucleoside polyphosphates useful in the instant disclosure is depicted in Structure 2 below,

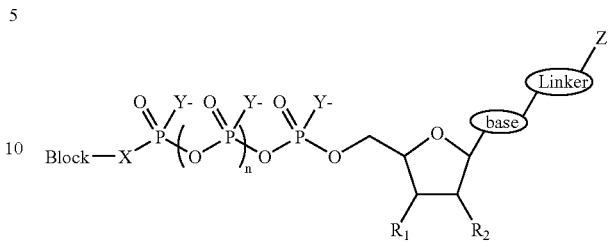

In the Structure above, n is 1 or greater; R1 and R2 are independently H, Cl, Br, F, I, SH, SR, $N_3$, $NH_2$, NHR, OR or OH; 'base' is a natural or modified nucleoside base; X is $CH_2$, O, S or NH; Y is O, S or $BH_3$; and 'Block' is an organic moiety containing at least one carbon atom and may contain heteroatoms as well as a detectable moiety. 'Block' may also be H when X is $CH_2$. The linker may be H, alkyl, alkenyl, alkynyl, aromatic, or heterocyclic and may contain atoms such as C, H, N, O, S, P and halogen. Z may be H or a detectable moiety such as a radioisotope, an electrochemical tag, a fluorescent tag, an energy transfer (ET) label, a mass spectrometry tag, a Raman tag, a hapten, a chemiluminescent group, an enzyme, a chromophore, and two or more labels. The label may also be charged, e.g. Cy3.5, Cy5.5, carboxyfluorescein, or a dye attached to a charged moiety, e.g., carboxyfluorescein attached to cysteic acid or similar charged species.

It has been discovered that when n is 2 or greater, the nucleotides are significantly better substrates for polymerases than when n is 1. Therefore, in preferred embodiments of the present invention, n is 2, 3 or 4. In more preferred embodiments of the present invention, X and Y are O, R1 and R2 are independently H or OH and Z is either H or a fluorescent label.

The molecule may be modified with a moiety which imparts an additional negative charge or a net positive charge to Structure 2 at physiological or nucleic acid sequencing conditions. The moiety may be any charged species which alters the electrophoretic mobility of the Structure, e.g., α-sulfo-β-alanine, cysteic acid, sulfonic acids, carboxylates, phosphates, phosphodiesters, phosphonates, amines, quarternized amines, and phosphonium moieties. The moiety (referred to as a "mobility modifier") may be attached between the linker and Z, between the base and linker, and may be attached only to the sugar or only to the linker. It may also be attached between terminal phosphate and block and may in fact be the terminal block. It may also be attached to the terminal block, if terminal block is labeled, between the label and terminal block or only to the label on terminal block. The molecule may also contain multiple linkers and moieties which are alternatively spaced together.

When the terminal phosphate blocked nucleic acid polyphosphate is a terminator, it migrates on separation media at different rate than the sequencing reaction products and result in improved sequence data (i.e., no blobs which obscure true data) and permit direct loading of nucleic acid sequencing reactions onto separating media.

Another embodiment of current invention involves the use of terminal phosphate blocked nucleoside polyphosphates in DNA or RNA amplification methods at high temperatures. Examples of such methods include polymerase chain reaction (PCR), rolling circle amplification (RCA), and nucleic acid sequence based amplification (NASBA). For e.g., wherein the target molecule is a nucleic acid polymer such as DNA, it may be amplified by PCR incorporation of a terminal phosphate blocked nucleotide base such as adenine, thymine, cytosine, guanine or other nitrogen heterocyclic bases into the DNA molecule. The polymerase chain reaction (PCR) method is described by Saiki et al in Science Vol. 239, page 487, 1988, Mullis et al in U.S. Pat. No. 4,683,195 and by Sambrook, J. et al. (Eds.), Molecular Cloning, second edition, Cold Spring Harbor Laboratory Press, Cold Spring Harbor, N.Y. (1980), Ausubel, F. M. et al. (Eds.), Current Protocols in Molecular Biology, John Wiley & Sons, Inc., NY (1999), and Wu, R. (Ed.), Recombinant DNA Methodology II, Methods in Enzymology, Academic Press, Inc., NY, (1995). Using PCR, the target nucleic acid for detection such as DNA is amplified by placing it directly into a reaction vessel containing the PCR reagents and appropriate primers. Typically, a primer is selected which is complimentary in sequence to at least a portion of the target nucleic acid.

It is noted that nucleic acid polymerase reactions suitable for amplifying nucleic acids may further include various RCA methods of amplifying nucleic acid sequences. For example, those disclosed in U.S. Pat. No. 5,854,033 to Lizardi, Paul M., incorporated herein by reference, are useful. Polymerase reactions may further include the nucleic acid sequence based amplification (NASBA) wherein the system involves amplification of RNA, not DNA, and the amplification is iso-thermal, taking place at one temperature (41° C.). Amplification of target RNA by NASBA involves the coordinated activities of three enzymes: reverse transcriptase, Rnase H, and T7 RNA polymerase along with oligonucleotide primers directed toward the sample target RNA. These enzymes catalyze the exponential amplification of a target single-stranded RNA in four steps: extension, degradation, DNA synthesis and cyclic RNA amplification.

The DNA sequence for amplification may include DNA isolated from cells, chemically treated DNA such as bisulfite treated methylated DNA or DNA chemically or enzymatically synthesized according to methods known in the art. Such methods include those described in DNA Structure Part A: Synthesis and Physical analysis of DNA, Lilley, D. M. J. and Dahlberg, J. E. (Eds.), Methods Enzymol., 211, Academic Press, Inc., New York (1992), which is herein incorporated by reference. The DNA sequence may further include chromosomal DNA and natural or synthetic oligonucleotides. The DNA may be either double- or single-stranded.

Another embodiment of the thermally stable terminal phosphate blocked nucleoside polyphosphates useful in the instant disclosure is depicted in Structure 3:

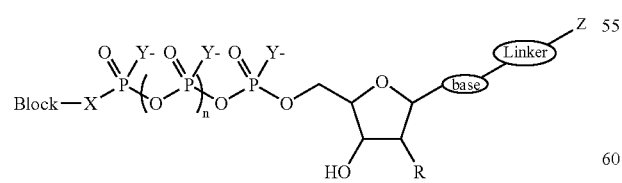

In the Structure above, n is 1 or greater; R is H, Cl, Br, F, I, SH, SR, N3, NH2, NHR, OR or OH; 'base' is a natural or modified nucleoside base; X is $CH_2$, O, S or NH; Y is O, S or $BH_3$; and 'Block' is an organic moiety containing atleast one carbon atom and may contain heteroatoms as well as a detectable moiety. 'Block' may also be H when X is $CH_2$. The linker may be H, alkyl, alkenyl, alkynyl, aromatic, or heterocyclic and may contain atoms such as C, H, N, O, S, P and halogen. Z may be H or a detectable moiety such as a radioisotope, an electrochemical tag, a fluorescent tag, an energy transfer (ET) label, a mass spectrometry tag, a Raman tag, a hapten, a chemiluminescent group, an enzyme, a chromophore, and two or more labels. The label may also be charged, e.g. Cy3.5, Cy5.5, carboxyfluorescein, or a dye attached to a charged moiety, e.g., carboxyfluorescein attached to cysteic acid or similar charged species.

It has been discovered that when n is 2 or greater, the nucleotides are significantly better substrates for polymerases than when n is 1. Therefore, in preferred embodiments of the present invention, n is 2, 3 or 4. In more preferred embodiments of the present invention, X and Y are O, R is H or OH and Z is either H or a fluorescent label.

In another preferred embodiment of the terminal phosphate blocked nucleotides of Structure 3 useful in the current invention, n is 2, 3 or 4, X and Y are O, block is a small C1-C10 alkyl, aryl with or without substituents, base is a naturally occurring base, linker is H and has no label attached to it, R is H or OH.

The molecule may be modified with a moiety that imparts an additional negative charge or a net positive charge to Structure 3 at physiological or nucleic acid sequencing conditions. The moiety may be any charged species which alters the electrophoretic mobility of the Structure, e.g., α-sulfo-β-alanine, cysteic acid, sulfonic acids, carboxylates, phosphates, phosphodiesters, phosphonates, amines, quarternized amines, and phosphonium moieties. The moiety (referred to as a "mobility modifier") may be attached between the linker and Z, between the base and linker, and may be attached only to the sugar or only to the linker. It may also be attached between terminal phosphate and block and may in fact be the terminal block. It may also be attached to the terminal block, if terminal block is labeled, between the label and terminal block or only to the label on terminal block. The molecule may also contain multiple linkers and moieties which are alternatively spaced together.

The methods of the present invention described above may include conducting the polymerase reaction in the presence of at least one of DNA or RNA polymerase. Suitable nucleotides for addition as substrates in the polymerase reaction include nucleoside polyphosphates, deoxynucleoside polyphosphates, and dideoxynucleoside polyphosphates, carbocyclic nucleoside polyphosphates and acyclic nucleoside polyphosphates and analogs thereof. Particularly desired are nucleotides containing 3, 4, or 5 phosphoryl groups in the polyphosphate chain, where the end phosphate is blocked.

EXAMPLES

The following examples illustrate certain preferred embodiments of the illustration but are not intended to be illustrative of all embodiments.

Example 1

Synthesis of Methyl-block Dye-labeled-2',3'-Dideoxynucleoside-5'-tetraphosphates: Synthesis of Fluorescein-18-ddA4P-Methyl

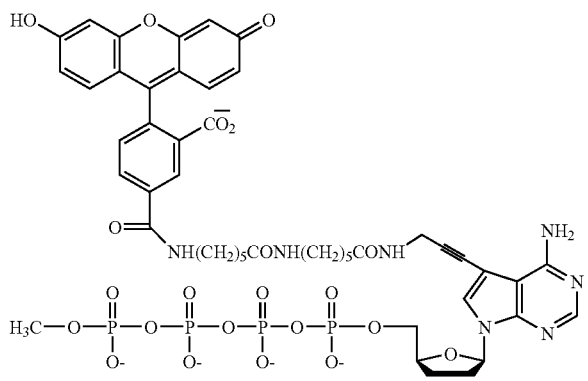

A. Preparation of FAM-18-ddATP

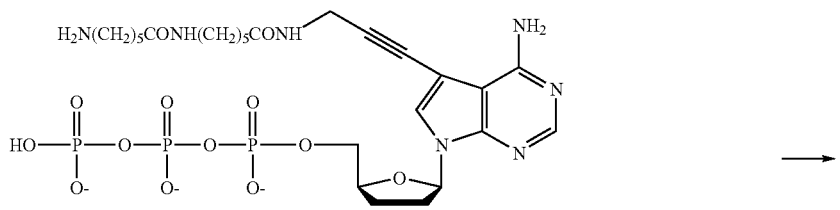

18-ddATP

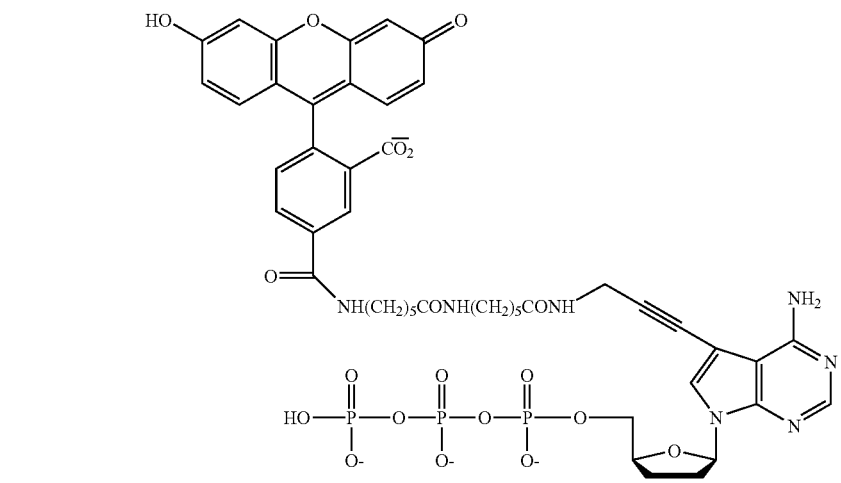

FAM-18-ddATP

A solution of 18-ddATP (60 μmoles, in 5 ml 0.1M NaHCO3/Na2CO3, pH 8.5) was cooled on an ice/water bath. To the solution was added 5-carboxy-fluorescein-NHS ester (35 mg, 1eq.) in DMF (5 ml). The reaction flask was removed from the cooling bath and the reaction mixture was stirred at room temperature for 16 hrs. The product purified by anion exchange chromatography and HPLC. The product containing fractions were concentrated then lyophilized to yield a yellow solid.

B. Preparation of Methyl-Phosphoimidazolidate

Methyl-monophosphate (50 μmol) was coevaporated with anhydrous DMF (2×2ml) and tributylamine (50 μmol). This was redissolved in anhy. DMF (0.5 ml) and treated with carbonyldiimidazole (200 μmol, 5 eq.) for overnight. The reaction mixture was quenched by addition of methanol (50 μl). After 1 hr. the mixture was evaporated to dryness in vacuum and redissolved in anhy. DMF (500 μl).

C. Synthesis of Fluorescein-18-ddA4P-Methyl

FAM-18-ddATP (3 μmol) was coevaporated with anhy. DMF and tributylamine and redissolved in anhy. DMF (400 μl). To this solution, 100 μl of methyl phosphoimidazolidate was added and the reaction mixture was stirred for overnight. The mass spectral analysis indicated the complete conversion of triphosphate to the required methyl tetraphosphate. The reaction mixture was concentrated and purified first on anion exchange column followed by X-terra C18 RP HPLC column. The required fraction were collected, concentrated in vacuo and redissolved in water. The yield was monitored spectroscopically as 2.5 μmol. UV max 501 nm, ESMS: 1204 (M-1).

Example 2

Synthesis of Energy Transfer Dye Based Blocked Dideoxynucleoside-5'-tetraphosphate:FAM-TAMRA-ddA4P-Methyl

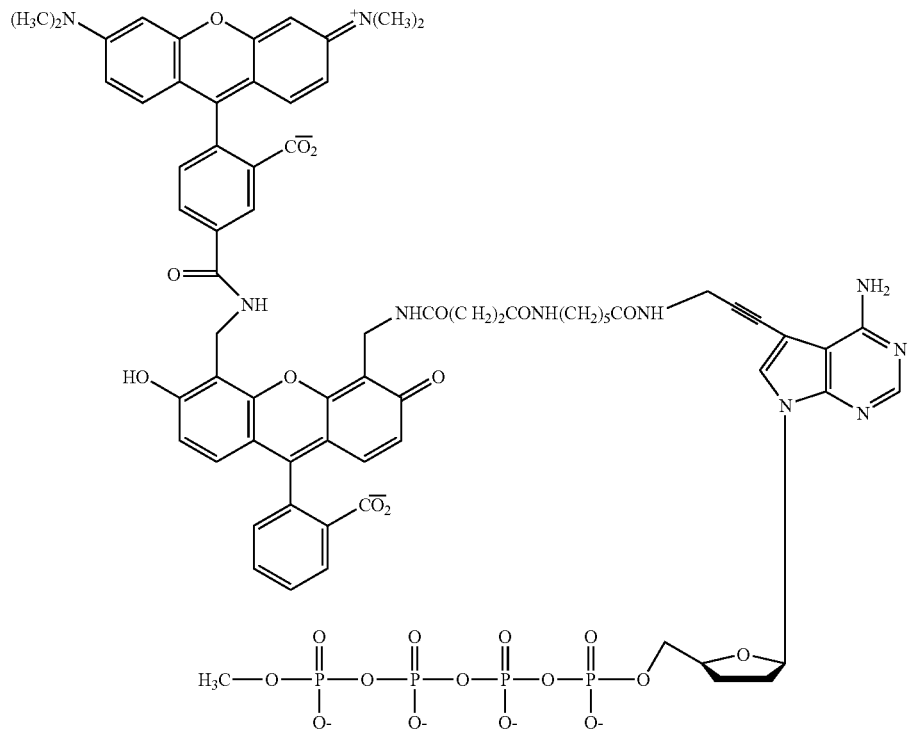

FAM-TAMRA-18-ddATP was converted to the methyl tetraphosphate essentially the same way as reported above for the synthesis of FAM-18-ddA4P-Methyl. The yield from 10 μmol of starting material was 8.5 μmol. UV 495 and 556 nm. ESMS: 1644 (M-1).

Example 3

Stability of Normal and Methyl Blocked Energy Transfer Terminator

Figure 2:
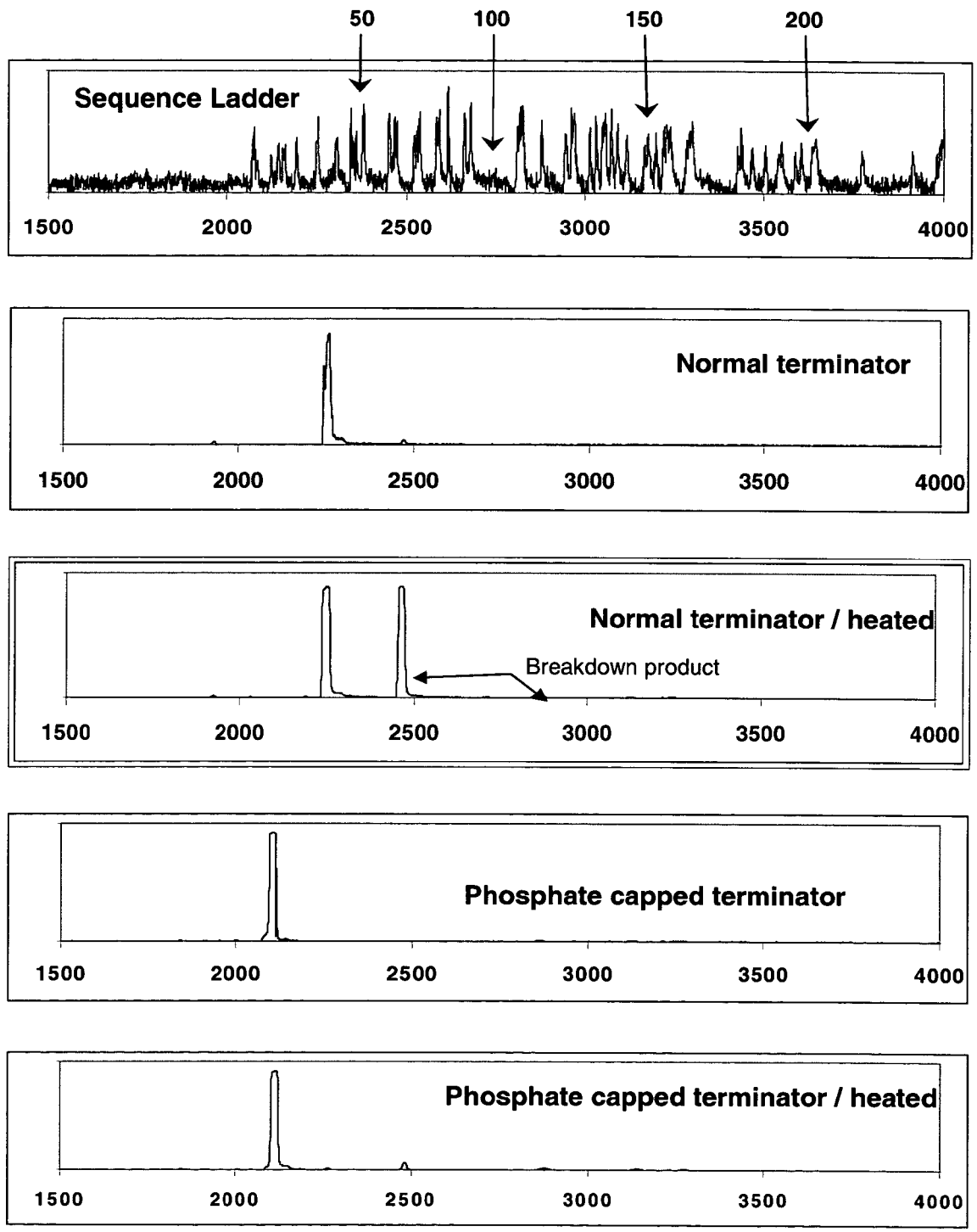
FIG. 2 shows the stability of normal terminator and terminal phosphate blocked terminator on heating at 95° C. for 20 minutes.

A sequence reaction containing 25 mM HEPES 8.0, 3 mM MgCl2, 1 mM MnSO4, 200 micromolar dNTP, 0.01% tween-20, 20 units Thermo Sequenase I, 0.8 milliunits pyrophosphatase, 100 ng M13mp18, 5 μmoles universal−40 primer, and 3.5 micromolar FAM-TAM-18-ddATP was cycled 25 times from 95 degrees C., 15 seconds to 60 degrees C., 2 minutes. The reaction was then ethanol precipitated and electrophoresed on a MegaBACE 1000 sequencing machine (FIG. 2, Panel 1). If it was not ethanol precipitated, the breakdown products would appear as blobs on electropherogram and would interfere with fragments between 50-100 nucleotides long.

On the same MegaBACE run, 10 micromolar FAM-TAM-18-ddATP or 10 micromolar FAM-TAM-18-ddA4P-methyl in 25 mM HEPES 8.0, 3 mM MgCl2, 1 mM MnSO4, 0.01% tween-20 was electrophoresed directly (without precipitation) with or without heating at 95 degrees C. for 20 minutes (Panel 2-5). It is clear from FIG. 2, Panels 2 & 3 that the normal terminator degrades on heating while the same terminator with methyl block at the terminal phosphate remain mostly intact, panels 4 and 5.

Example 4

DNA Sequencing Using Normal and Terminal Phosphate Blocked Terminator

Figure 3:
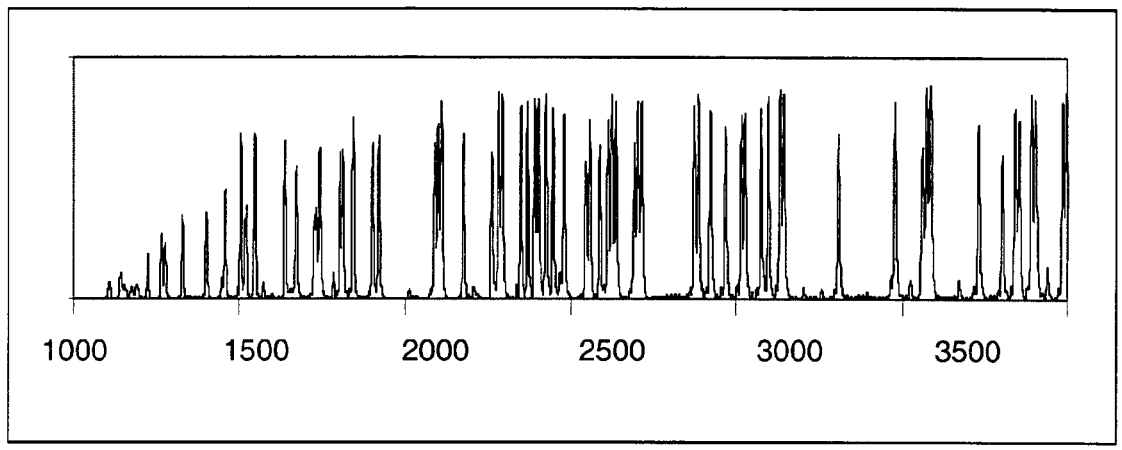
FIG. 3 shows the sequencing ladder obtained using either the normal energy transfer terminator or the terminal phosphate blocked terminator
Figure 3:
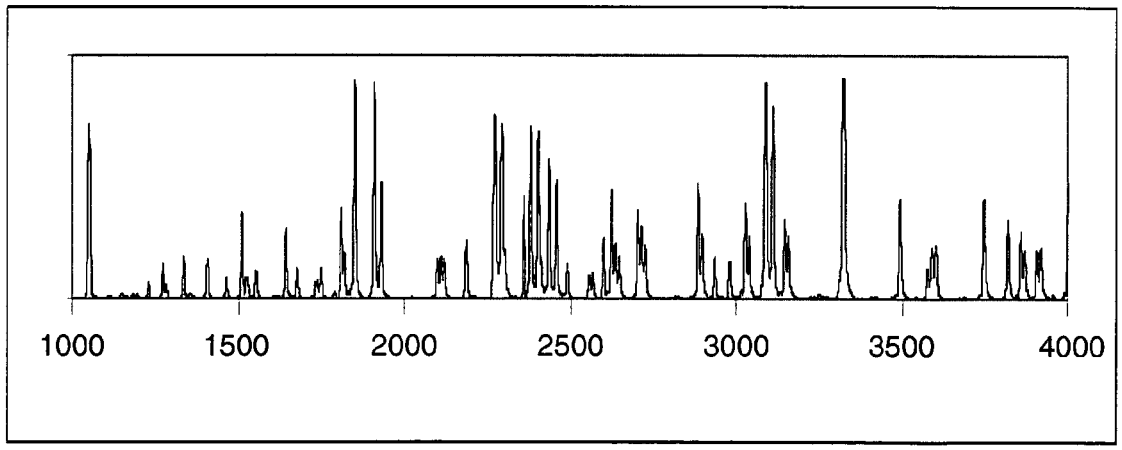

Sequence reactions contained 25 mM HEPES 8.0, 3 mM MgCl2, 1 mM MnSO4, 200 micromolar dNTP, 0.01% tween-20, 20 units Thermo Sequenase I, 0.8 milliunits pyrophosphatase, 100 ng M13mp18, 5 μmoles universal−40 primer, and 3.5 micromolar FAM-TAM-18-ddATP or 50 micromolar FAM-TAM-18-ddA4P-methyl as indicated. Reactions were cycled 25 times from 95 degrees C., 15 seconds to 60 degrees C., 2 minutes. Reactions were then ethanol precipitated and electrophoresed on an ABI377 DNA sequencing machine. It is clear from FIG. 3 that the methyl blocked terminator gave similar sequence ladder in comparison with the normal terminator.

Example 5

Figure 4:
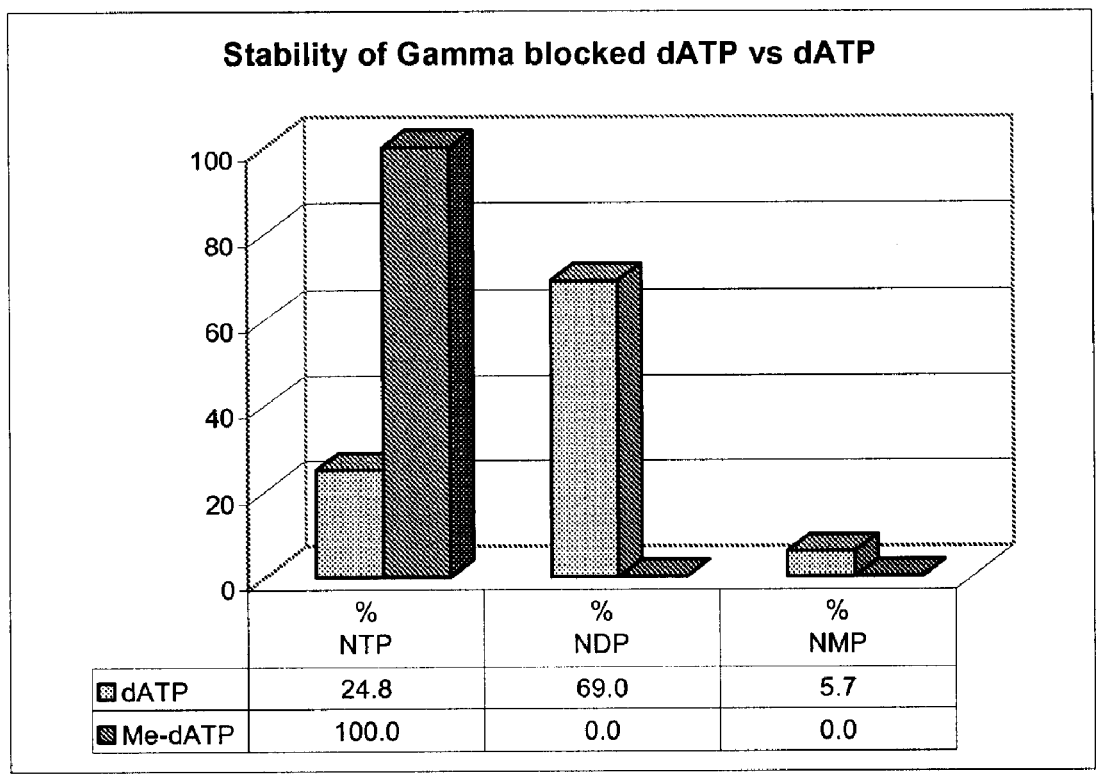
FIG. 4 shows the stability of normal and gamma blocked nucleoside triphosphates on heating at 95° C. for 2 hours.

Stability of γ-blocked Nucleoside Triphosphates dATP and γ-methyl-dATP were separately dissolved in 100 μl buffer (25 mM Tris, pH 8, 5 mM MgCl2, 2 mM DTT and 10% glycerol) at 50 μM concentration and heated at 95° C. for 2h. Reaction mixture was analyzed by reverse phase HPLC for any decomposition products and by LCMS for the identification of products. Both HPLC and LCMS showed no decomposition of γ-methyl-dATP, while dATP had decomposed by ca 75% to dADP (69.0%) and dAMP (5.7%) (FIG. 4).

Example 6

Stability of γ-DDAO-ddTTP

Figure 5:
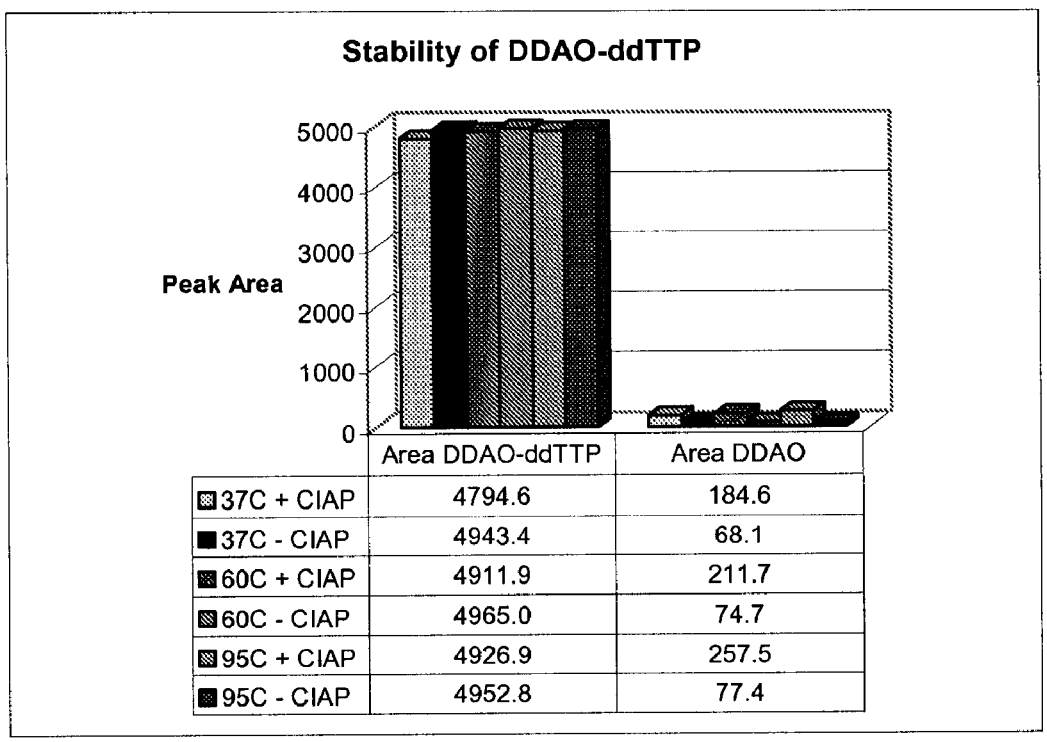
FIG. 5 shows the stability of γ-DDAO-ddTTP.

Three sets of two samples (100 μl each) were prepared by dissolving γ-DDAO-ddTTP in a Tris buffer (25 mM Tris, pH 8, 5 mM MgCl2, 2mM DTT and 10% Glycerol) at 50 μM concentration. Each set was heated at 37° C., 60° C. or 95° C. for 10 minutes. To one sample from each set, one unit of Calf Intestinal Alkaline Phosphatase (CIAP) was added and mixture was incubated at 37° C. for 5 minutes. A unit of CIAP hydrolyzes 1 μmol of p-nitrophenyl-phosphate per minute. Samples without CIAP were also incubated at 37° C. for 5 minutes. All samples were then analyzed by HPLC. Neither temperature nor CIAP had any significant affect on the stability of γ-DDAO-ddTTP. Slight increase in free dye formation in the presence of CIAP compared to non-CIAP treated sample is probably due to the decomposition of impurities in the starting material (FIG. 5).

Having described the particular, desired embodiments of the invention herein, it should be appreciated that modifications may be made there through without departing from the contemplated scope of the invention. The true scope of the invention is set forth in the claims appended hereto.

What is claimed is:

1. In a method for nucleic acid analysis, which includes a high temperature polymerase reaction of a nucleic acid template, a primer, a nucleic acid polymerase, and at least one nucleoside polyphosphate, the improvement comprising conducting said polymerase reaction in the presence of at least one thermally stable terminally blocked nucleoside polyphosphates, wherein said nucleic acid analysis is chain terminator DNA sequencing.

2. The method of claim 1, wherein said terminally blocked nucleoside polyphosphate is a labeled terminator.

3. The method of claim 1, wherein said at least one terminally blocked nucleoside polyphosphate has additional negative charges.

4. The method of claim 1, wherein said at least one terminally blocked nucleoside polyphosphate is net positively charged.

5. The method of claim 1, wherein said terminally blocked nucleoside polyphosphates are represented by the formula

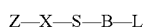

wherein

Z is a terminal block consisting of an organic moiety, including linear or branched, cyclic or acyclic alkyl, alkenyl, alkynyl, aromatic, heterocycle or a detectable label;

X is a polyphosphate chain with at least 3 phosphate or modified phosphate groups;

S is a natural or modified sugar, a carbocycle, or an acyclic linker;

B is a natural or modified heterocyclic base; and

L is H or a linker moiety selected from the group consisting of substituted or unsubstituted, linear or branched cyclic or acyclic alkyl, alkenyl, alkynyl, aromatic, or heterocyclic.

6. The method of claim 5, wherein at least one of L, B, S, X or Z is substituted with a detectable moiety.

7. The method of claim 5, wherein at least one of L, B, S, X or Z is substituted with a negatively charged moiety.

8. The method of claim 5, wherein at least one of L, B, S, X or Z is substituted with a moiety that impart a net positive charge.

9. The method of claim 5, wherein Z is modified to contain additional negative charges or one or more positive charges.

10. The method of claim 5, wherein L is labeled with a detectable moiety selected from the group consisting of radioisotopes, electrochemical tags, fluorescent tags, energy transfer (ET) labels, mass spectrometry tags, Raman tags, haptens, chemiluminescent groups, enzymes, chromophores, and any combinations thereof.

11. The method of claim 5, wherein B is selected from the group consisting of uracil, cytosine, guanine, adenine, thymine, 7-deazaguanine, 7-deazaadenine, hypoxanthine, 7-deazahypoxanthine and 2,6-diaminopurine or derivatives thereof.

12. The method of claim 5, wherein X is a polyphosphate chain of 3, 4 or 5 phosphate groups.

13. The method of claim 5 for sequencing, wherein S is selected from the group consisting of 2'-deoxyribosyl, 3'-deoxyribosyl, 2, 3'-dideoxyribosyl, 2', 3'-dideoxy-2', 3'-didehydroribosyl, 3'-alkoxyribosyl, 3'-azidoribosyl, 3'-aminoribosyl, 3'-fluororibosyl, 3'-mercaptoribosyl, 3'-alkylthioribosyl, 2'-alkoxyribosyl, 2'-azidoribosyl, 2'-aminoribosyl, 2'-fluororibosyl, 2'-mercaptoribosyl, 2'-alkylthioribosyl, carbocyclic, acyclic and other modified sugars.

14. The method of claim 5, wherein said terminally blocked nucleoside polyphosphate is represented by the formula

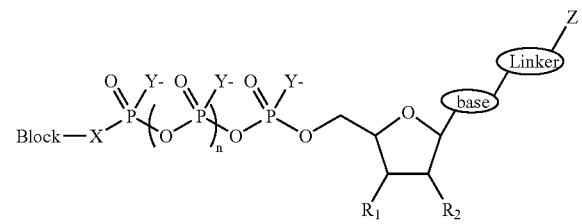

Where n is 1, 2 or 3;

Block is an organic moiety or H when X is $CH_2$;

X is $CH_2$, O, S or NH;

Y is O, H or $BH_3$;

R is H or OH;

Base is a natural or modified nucleoside base;

Linker is H, alkyl, aryl, alkylaryl, alkenyl, alkynyl, aromatic, or heterocyclic and may optionally be charged; and Z is a fluorescent dye, an energy transfer dye, a chemiluminescent compound, a colored compound, a mass tag or no label at all.

* * * * *